United States Patent
Omotowa

(10) Patent No.: US 7,638,659 B2
(45) Date of Patent: *Dec. 29, 2009

(54) PROCESSES FOR PRODUCING CHLOROFLUOROCARBON COMPOUNDS USING INORGANIC FLUORIDE

(75) Inventor: Bamidele Omotowa, Idaho Falls, ID (US)

(73) Assignee: International Isotopes, Inc., Idaho Falls, ID (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/853,541

(22) Filed: Sep. 11, 2007

(65) Prior Publication Data

US 2008/0262274 A1 Oct. 23, 2008

Related U.S. Application Data

(60) Provisional application No. 60/912,564, filed on Apr. 18, 2007.

(51) Int. Cl.
*C07C 19/08* (2006.01)

(52) U.S. Cl. .................................................... 570/170

(58) Field of Classification Search ........................ None
See application file for complete search history.

(56) References Cited

U.S. PATENT DOCUMENTS

| | | | |
|---|---|---|---|
| 4,070,439 A | 1/1978 | Osaka et al. | |
| 4,876,406 A * | 10/1989 | Foulletier | 570/165 |
| 5,091,602 A | 2/1992 | Park et al. | |
| 5,399,549 A | 3/1995 | Felix et al. | |
| 5,399,796 A | 3/1995 | Correia et al. | |
| 5,446,216 A | 8/1995 | Rao | |
| 5,545,770 A | 8/1996 | Rao | |
| 5,831,136 A | 11/1998 | Rao | |
| 5,841,006 A | 11/1998 | Cuzzato et al. | |
| 5,918,106 A | 6/1999 | Bulko et al. | |
| 6,074,985 A | 6/2000 | Elsheikh et al. | |
| 6,127,586 A | 10/2000 | Scott et al. | |
| 6,232,514 B1 | 5/2001 | Cuzzato et al. | |
| 6,268,541 B1 | 7/2001 | Kono et al. | |
| 6,392,106 B1 | 5/2002 | Kono et al. | |
| 6,433,233 B1 | 8/2002 | Kanemura et al. | |
| 6,479,718 B1 | 11/2002 | Elsheikh et al. | |
| 6,503,865 B1 | 1/2003 | Kanemura et al. | |
| 6,841,705 B2 | 1/2005 | Yuichi et al. | |
| 7,067,707 B2 | 6/2006 | Piepho et al. | |
| 7,071,368 B1 | 7/2006 | Merkel et al. | |
| 7,074,973 B2 | 7/2006 | Nappa et al. | |
| 2001/0049457 A1 * | 12/2001 | Stephens | 570/123 |

OTHER PUBLICATIONS

Okazaki et al., Kogyo Kagaku Zasshi (1969), 72(3), 630-3.*
Park et al., Kongop Hwahak (1993), 4(2)m 318-23.
Schumb, W.C., "Some Metathetical Reactions of the Gaseous Fluorides of Group IV," Journal of the American Chemical Society, vol. 74, Jun. 1951, pp. 1754-1760.
U.S. NonFinal Office Action dated Apr. 11, 2008 under U.S. Appl. No. 11/853,521, 8 pages.
U.S. NonFinal Office Action dated Mar. 14, 2008 under U.S. Appl. No. 11/853,557, 8 pages.
U.S. NonFinal Office Action dated Mar. 14, 2008 under U.S. Appl. No. 11/853,572, 8 pages.

* cited by examiner

*Primary Examiner*—Karl J Puttlitz
(74) *Attorney, Agent, or Firm*—Perkins Coie LLP

(57) ABSTRACT

Methods and systems for producing chlorofluorocarbon with an inorganic fluoride (e.g., germanium tetrafluoride ($GeF_4$)) are disclosed herein.

25 Claims, 8 Drawing Sheets

US 7,638,659 B2

PROCESSES FOR PRODUCING CHLOROFLUOROCARBON COMPOUNDS USING INORGANIC FLUORIDE

CROSS-REFERENCE TO RELATED APPLICATION

This application claims priority to Provisional U.S. Patent Application No. 60/912,564, entitled "Processes for Production of Hydrofluorocarbon Using Inorganic Fluoride From Hexachloroethane," filed Apr. 18, 2007, the disclosure of which is incorporated herein by reference in its entirety. This application is also related to U.S. patent application Ser. No. 11/853,572, entitled "Processes for Producing Halogenated Hydrocarbon Compounds Using Inorganic Fluoride", U.S. patent application Ser. No. 11/853,521, entitled "Processes for Producing Hydrofluorocarbon Compounds Using Inorganic Fluoride", and U.S. patent application Ser. No. 11/853,557, entitled "Processes for Producing Halocarbon Compounds Using Inorganic Fluoride", the disclosures of which are incorporated herein by reference in their entirety

TECHNICAL FIELD

The present disclosure is related to processes for producing halocarbon compounds (e.g., chlorofluorocarbon compounds). In particular, the present disclosure is related to processes for producing chlorofluorocarbon compounds, such as 1,1,2-trichloro-1,2,2-trifluoroethane (CFC-113), 1,1-dichloro-1,2,2-trifluoroethane (CFC-114a), and/or 1-chloro-1,1,2,2,2-pentafluoroethane (CFC-115).

BACKGROUND

Chlorofluorocarbon (CFC) and hydrochlorofluorocarbon (HCFC) compounds have been used as refrigerants, fire extinguishing agents, propellants, and solvents since the early twentieth century. However, CFC and HCFC are now believed to deplete the ozone layer of the earth via UV-promoted reactions. As a result, the U.S. Environmental Protection Agency has already banned the production and importation of certain CFC and HCFC products.

Internationally, the Montreal Protocol has set out plans for replacing CFC and HCFC compounds with hydrofluorocarbon (HFC) compounds. However, the cost of producing HFC compounds is considerably higher than that of producing CFC or HCFC compounds. Presently, industrial fluorination processes for producing HFC are based on hydrogen fluoride (HF) fluorination of chlorocarbons. FIG. 1 presents examples of known potential multistep routes to produce CFC-113.

As illustrated in FIG. 1, HFC-125 can be produced with either 1,1,2-trichloroethene (triclene) or 1,1,2,2-tetrachloroethene (perclene) using multistep processes. For example, HFC-125 can be produced by first converting either triclene or perclene into 1,1-dichloro-2,2,2-trifluoroethane (HCFC-123) and then fluorinating HCFC-123 to 1-chloro-1,2,2,2-tetrafluoroethane (HCFC-124). HFC-125 can then be produced by performing chlorine-fluorine exchange on HCFC-124 with hydrogen fluoride.

The processes for producing HFC-125 are more complex, both chemically and operationally, than those for CFC and HCFC compounds. Moreover, both the triclene and perclene processes require disposing of hydrogen chloride (HCl) byproducts. Procedures and equipment are available to convert some of the HCl byproducts into a chlorine ($Cl_2$) gas and subsequently recycle the chlorine gas back into the production process. Nonetheless, this recycling operation adds to the cost of the overall HFC production process.

DETAILED DESCRIPTION

Figure 1:
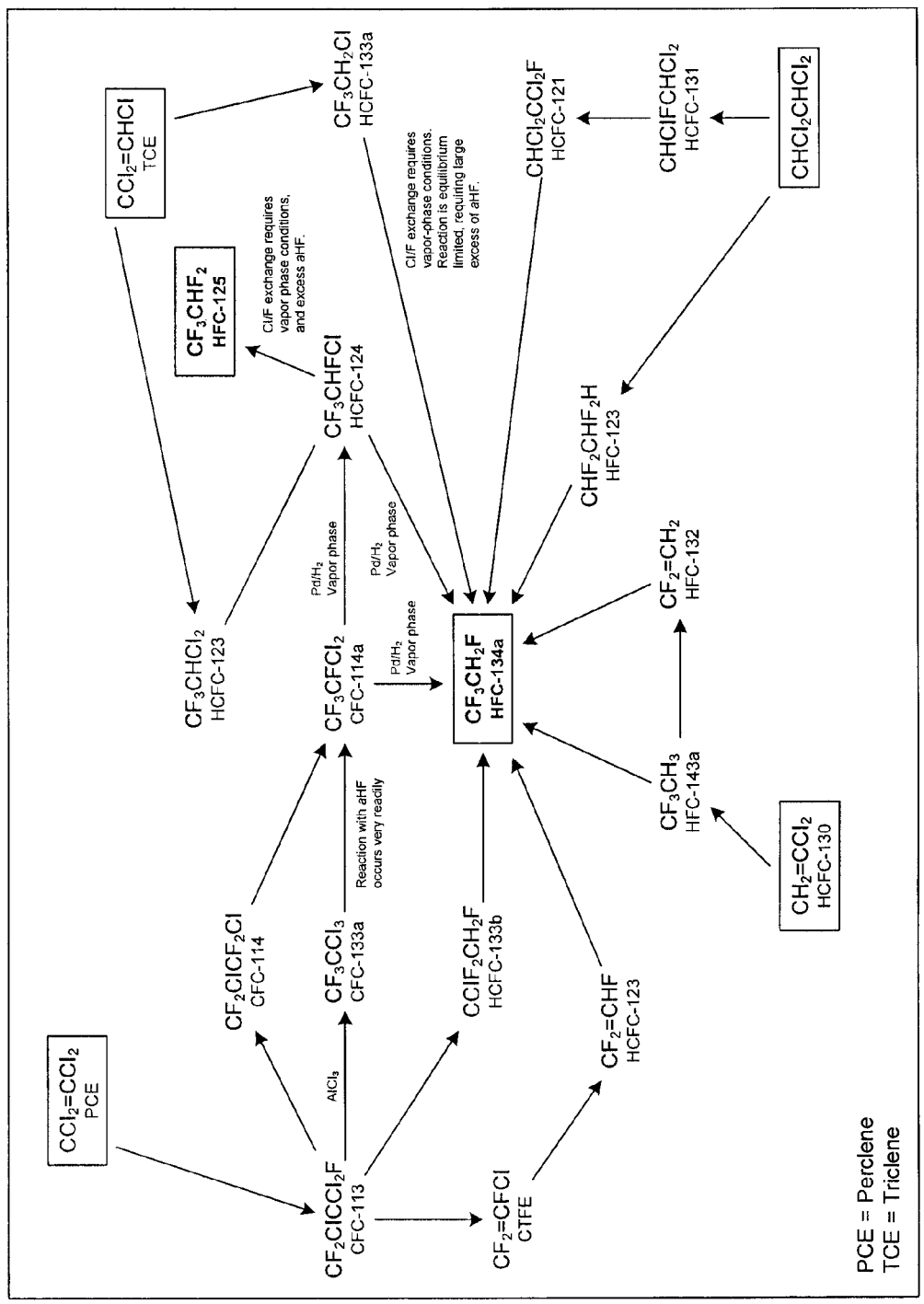
FIG. 1 is a schematic diagram illustrating potential routes to HFC-125 and HFC-134a in accordance with the prior art.

Specific details of several embodiments of the disclosure are described below with reference to processes for efficiently and cost-effectively producing halogenated hydrocarbon compounds. The term "halocarbon compounds" generally refers to halogen-substituted (e.g., fluorine-, chlorine-, bromine-, and/or iodine-substituted) organic compounds containing only carbon and halogen. Examples of halocarbon compounds include fluorocarbon compounds containing fluorine and carbon, chlorocarbon compounds containing chlorine and carbon, and chlorofluorocarbon compounds containing fluorine, chlorine, and carbon. Several other embodiments of the invention may have different configurations, components, or procedures than those described in this section. A person of ordinary skill in the art, therefore, will accordingly understand that the invention may have other embodiments with additional elements, or the invention may have other embodiments without several of the elements shown and described below.

One aspect of the present disclosure is directed to the use of an inorganic fluoride as a fluorinating agent for producing chlorofluorocarbon (CFC) compounds, in particular, CFC-113 ($CCl_2FCClF_2$). The following description uses germanium tetrafluoride ($GeF_4$) as an example of an inorganic fluoride to show various embodiments of the fluorination reaction of the present disclosure for illustration purposes. However, a skilled artisan will appreciate that $GeF_4$ is merely an example of an inorganic fluoride. Other inorganic fluoride for use in the systems and processes can include at least one of bromine trifluoride ($BrF_3$), manganese tetrafluoride ($MnF_4$), sulfur tetrafluoride ($SF_4$), bromine pentafluoride ($BrF_5$), and tungsten hexafluoride ($WF_6$).

Another aspect of the present disclosure relates to producing CFC-113, CFC-114a, and/or CFC-115 by performing a chlorine-fluorine exchange on chlorocarbon compounds. In one embodiment, the present disclosure relates to producing CFC-113 from 1,1,1,2,2,2-hexachloroethane (referred to as "hexachloroethane" hereinafter). The inventor has observed that the reaction described above has an unexpectedly high yield (about 70%-75%) and a good selectivity toward CFC-113, CFC-114a, CFC-115, and/or other desired chlorocarbon compounds, as described in more detail below with reference to the experimental results.

A further aspect of the present disclosure is directed to using one or more catalysts to catalyze a fluorination reaction between an inorganic fluoride and a chlorocarbon compound. It is believed that, in certain embodiments, the class of compounds known as superacids and/or Lewis acids can catalyze such fluorination reaction. The term "superacid" generally refers to an acid with an acidity greater than that of 100% sulfuric acid ($H_2SO_4$). Examples of superacids include trifluoromethane sulfonic acid ($CF_3SO_3H$) and fluorosulfuric acid ($FSO_3H$). The term "Lewis acid" generally refers to a compound that is an electrophile or an electron acceptor. Examples of Lewis acids include aluminum trichloride ($AlCl_3$), iron trichloride ($FeCl_3$), boron trifluoride ($BCl_3$), niobium pentachloride ($NbCl_5$), and the lanthanide triflates, e.g., ytterbium(III) triflate. In certain embodiments, aluminum trichloride ($AlCl_3$) can be used to react with $GeF_4$ to form $AlCl_xF_y$ (x+y=3), in situ, which has been observed to catalyze the $GeF_4$ fluorination of chlorocarbons. In other embodiments, $SbCl_3$, $SbF_5$, $SbF_3$, $AsF_5$, $AsCl_3$, $TaCl_5$, $TaF_5$, $NbCl_5$, $NbF_5$, $HSO_3F$, $CF_3SO_3F$, $Cr_2O_3$, and/or other suitable superacids and/or Lewis acids can also be used to catalyze a fluorination of chlorocarbons in the presence of, e.g., $GeF_4$.

Reaction Systems

Figure 2:
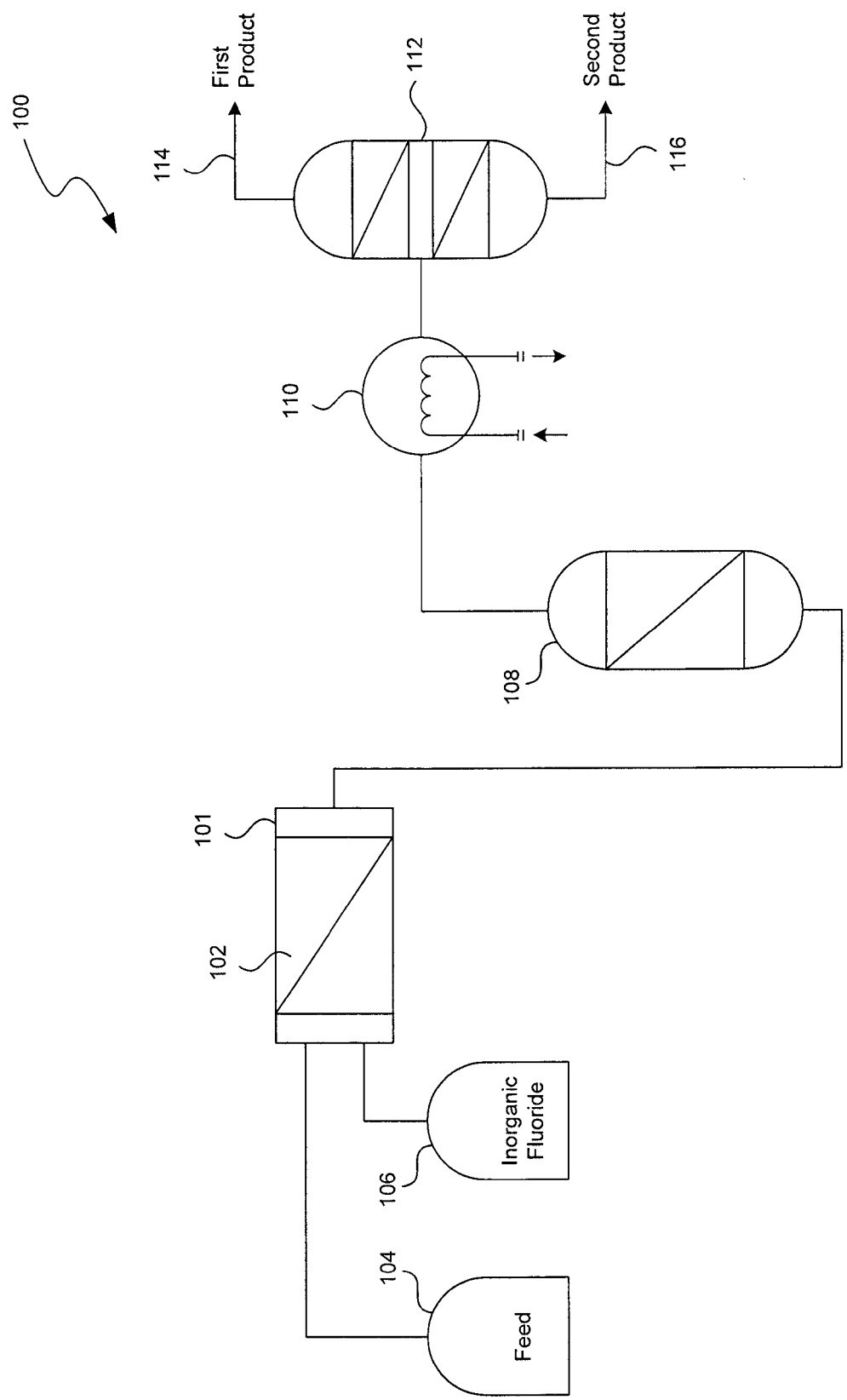
FIG. 2 is a schematic diagram illustrating a system for producing halocarbon compounds in accordance with an embodiment of the disclosure.

FIG. 2 is a schematic diagram illustrating a system 100 for producing halocarbon compounds in accordance with an embodiment of the disclosure. The system 100 can include a reactor 101 operatively coupled to a feed storage 104 containing, e.g., hexachloroethane, and an inorganic fluoride storage 106 containing, e.g., $GeF_4$. The reactor 101 can be configured generally as a tubular reactor constructed from Inconel, Hastelloy, and/or other fluorine-resistant material. In some embodiments, the reactor 101 can include a catalyst bed 102 containing $AlCl_3$ or other suitable catalyst. In other embodiments, the catalyst bed 102 can be omitted from the reactor 101, and a catalyst (e.g., $AlCl_3$) can be fed into the reactor 101 during operation.

The system 100 can include a scrubber 108 that receives a reaction product from the reactor 101. The scrubber 108 can be configured to remove impurities and/or unreacted material from the product. For example, in one embodiment, the scrubber 108 includes a liquid base containing, e.g., potassium hydroxide (KOH), sodium hydroxide (NaOH), and/or other bases for absorbing, reacting, and/or otherwise combining with unreacted inorganic halide (e.g., $GeF_4$). In another embodiment, the scrubber 108 includes a solid base (e.g., pellets) containing KOH, NaOH, and/or other bases. In further embodiments, the scrubber 108 can include both a liquid base and a solid base for removing unreacted halides.

The system 100 can also include an optional product trap 110 downstream of the scrubber 108 for collecting CFC and/or other compounds in the reaction product. In the illustrated embodiment, the product trap 110 is configured as a heat exchanger that can cool the reaction product with a coolant (e.g., liquid nitrogen). In some embodiments, heat exchange with the coolant substantially condenses the CFC and/or other compounds in the reaction product. In other embodiments, only a portion of the CFC and/or other compounds (e.g., materials with low boiling points) is condensed.

The system 100 can further include a separator 112 downstream of the optional product trap 110. The separator 112 can be configured to split CFC and/or other compounds in the reaction product. In the illustrated embodiment, the separator 112 includes a distillation column that can produce a first product from a top end 114 and a second product from a bottom end 116. In other embodiments, the separator 112 can also include a flash tank, a cyclone, and/or other liquid-liquid separation/liquid-gas separation devices. In further embodiments, instead of producing the first and second products from the top end 114 and the bottom end 116, the separator 112 can also produce products from locations intermediate the top end 114 and the bottom end 116 based on the volatility profile of the reaction product.

In operation, the reactor 101 first receives a reaction feed containing, for example, hexachloroethane from the feed storage 104 and an inorganic fluoride (e.g., $GeF_4$) from the inorganic fluoride storage 106. In one embodiment, $GeF_4$ can be in the stoichiometric amount required to fluorinate hexachloroethane in the reaction feed. For example, the molar ratio of $GeF_4$ to hexachloroethane can be about 1.16:1. In other embodiments, $GeF_4$ can be in molar excess of the stoichiometric amount required. For example, the molar ratio of $GeF_4$ to hexachloroethane in the reaction feed can be from about 2:1 to about 4:1.

In the reactor 101, $GeF_4$ and hexachloroethane in the reaction feed contact the catalyst (e.g., $AlCl_3$) held in the catalyst bed. The reactor 101 can be at a temperature of about 220° to about 375° C. and at a pressure of about 500 to 800 psig (i.e., about 3.45 MPa to about 5.52 MPa). In one embodiment, the inventor has observed that hexachloroethane and $GeF_4$ in the reaction feed can react to form CFC-113 with high yield and good selectivity at a reaction temperature of about 310° C. and a molar ratio of hexachloroethane to $GeF_4$ of about 1:1.67. Other potential fluorination products can include 1,1,1-trichloro-2,2,2-trifluoroethane (CFC-113a), 1,2-dichloro-1,2,2,2-tetrafluoroethane (CFC-114a), 1-chloro-1,1,2,2,2-pentafluoroethane (CFC-115), and/or other fluorine-substituted chloroethanes. In another embodiment, the inventor has observed that hexachloroethane and $GeF_4$ in the reaction feed can react to form CFC-114a (about 73%) and CFC-115 (about 27%) at a reaction temperature of about 340° C. and a molar ratio of hexachloroethane to $GeF_4$ of about 1:2.75.

There have been prior unsuccessful attempts to use $GeF_4$ for fluorination of chlorocarbons such as hexachloroethane. The inventor has recognized that those prior experiments failed, at least in part, because of the omission of an appropriate catalyst. The inventor has also recognized that $AlCl_3$ and/or other Lewis acid catalysts can cause $GeF_4$ to readily react with hexachloroethane. Without being bound by theory, it is believed that $GeF_4$ can first react with $AlCl_3$ to form a series of equilibria between $AlCl_3$ and $GeF_4$ as follows:

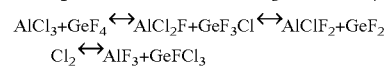

$$Cl_2 \leftrightarrow AlF_3 + GeFCl_3$$

It is believed that the $AlCl_xF_y$ (x+y=3) compounds may then act as Lewis acid catalysts to lower the activation energy for fluorinating hexachloroethane. It is also believed that $AlF_3$ is a more efficient catalyst than $AlCl_2F$ and/or $AlClF_2$. Thus, in some embodiments, the reaction equilibria can be shifted toward $AlF_3$ by, for example, adding excess $GeF_4$ to the reaction feed, removing products from the reaction, and/or using other suitable techniques.

In one embodiment, the reaction described above can be carried out in a batch mode. For example, the reaction conditions can be maintained in the reactor 101 until the reaction is complete, and then the reaction product can be discharged from the reactor 101 to the scrubber 108. In other embodiments, the reaction described above can be carried out in a continuous mode. For example, the reactor 101 can be configured as a plug-flow reactor, a constantly stirred tank reactor, and/or other types of reactor with sufficient residence time to allow the completion of the reaction in a continuous operation.

After the reaction is complete, the reaction product flows from the reactor 101 to the scrubber 108 for removing impurities and/or unreacted material from the product. For example, the scrubber 108 can remove germanium tetrachloride ($GeCl_4$) from other gaseous material in the reaction product. In another example, if $GeF_4$ is in molar excess of hexachloroethane in the reaction feed, some $GeF_4$ is likely to remain after the reaction is complete. In one embodiment, the scrubber 108 can contain KOH and/or NaOH that reacts with the excess $GeF_4$ in order to purify the reaction product. In other embodiments, the scrubber 108 can remove the excess $GeF_4$ using other physical and/or chemical techniques.

The reaction product can then pass through the optional product trap 110 for collecting CFC and/or other compounds. In the illustrated embodiment, the reaction product exiting the scrubber 108 can include a gas containing CFC-113, CFC-113a, CFC-114a, and/or CFC-115. When the reaction product passes through the product trap 110, CFC-113, CFC-113a, CFC-114a, CFC-115, and/or other chlorocarbon compounds in the reaction product can be substantially condensed by a coolant (e.g., liquid nitrogen). In other embodiments, the product trap 110 can include a refrigeration unit, an isotropic expander, an isenthalpic expander, and/or other cooling techniques for condensing the chlorocarbon compounds in the reaction product. In further embodiments, the system 100 can operate at a sufficient pressure (e.g., 1000 psig) such that the reaction product is at least partially a liquid at the outlet of the scrubber 108, and the product trap 110 can be omitted.

After the reaction product is substantially condensed, the separator 112 splits various chlorocarbon compounds (e.g., CFC-113) from others in the reaction product. In one embodiment, the separator 112 can produce the first product containing essentially CFC-113 from the top end 114 and the second product containing other CFC compounds (e.g., CFC-113a) from the bottom end 116. In another embodiment, the separator 112 can produce the first product containing CFC-115 and the second product containing CFC-114a. At one atmospheric pressure, CFC-113 has a boiling point of about 4° C., and CFC-113a has a boiling point of about 45.8° C. CFC-114a and CFC-115 have boiling points of about −73° C. and about −36° C., respectively. As a result, the relative volatility between CFC-113a and CFC-113 and that between CFC-114a and CFC-115 are sufficient to enable a ready separation of these two compounds.

Fluorination reaction carried out in the system 100 described above can efficiently and cost-effectively produce desired chlorocarbon compounds (e.g., CFC-113, CFC-114a, CFC-115, and/or other chlorofluorocarbon compounds) that can be used as precursors for producing HFC and/or HCFC compounds such as HFC-125 and HFC-134a. Unlike conventional techniques, using the system 100 can produce these chlorocarbon compounds via direct chlorine-fluorine exchange on hexachloroethane. The reaction has been observed to produce an unexpectedly high yield of at least about 70%, more preferably at least about 75%, and even more preferably at least about 80%. In one embodiment, the reaction has also been observed to produce a good selectivity toward CFC-113. In another embodiment, the reaction has been observed to produce a good selectivity toward CFC-114a of at least about 1.6, more preferably about 2.7, and even more preferably about 4.0. Moreover, the reaction, in one embodiment, has been observed to produce only CFC-114a and CFC-115, which have sufficiently different volatilities to enable ready separation of the reaction product.

Even though the system 100 described above has a one-pass configuration, in certain embodiments, the system 100 can also have at least one recycle loop. For example, in some embodiments, unreacted reaction feed and/or other compounds can be recycled back to the reactor 101.

Method for Producing Halocarbon Compounds

Figure 3:
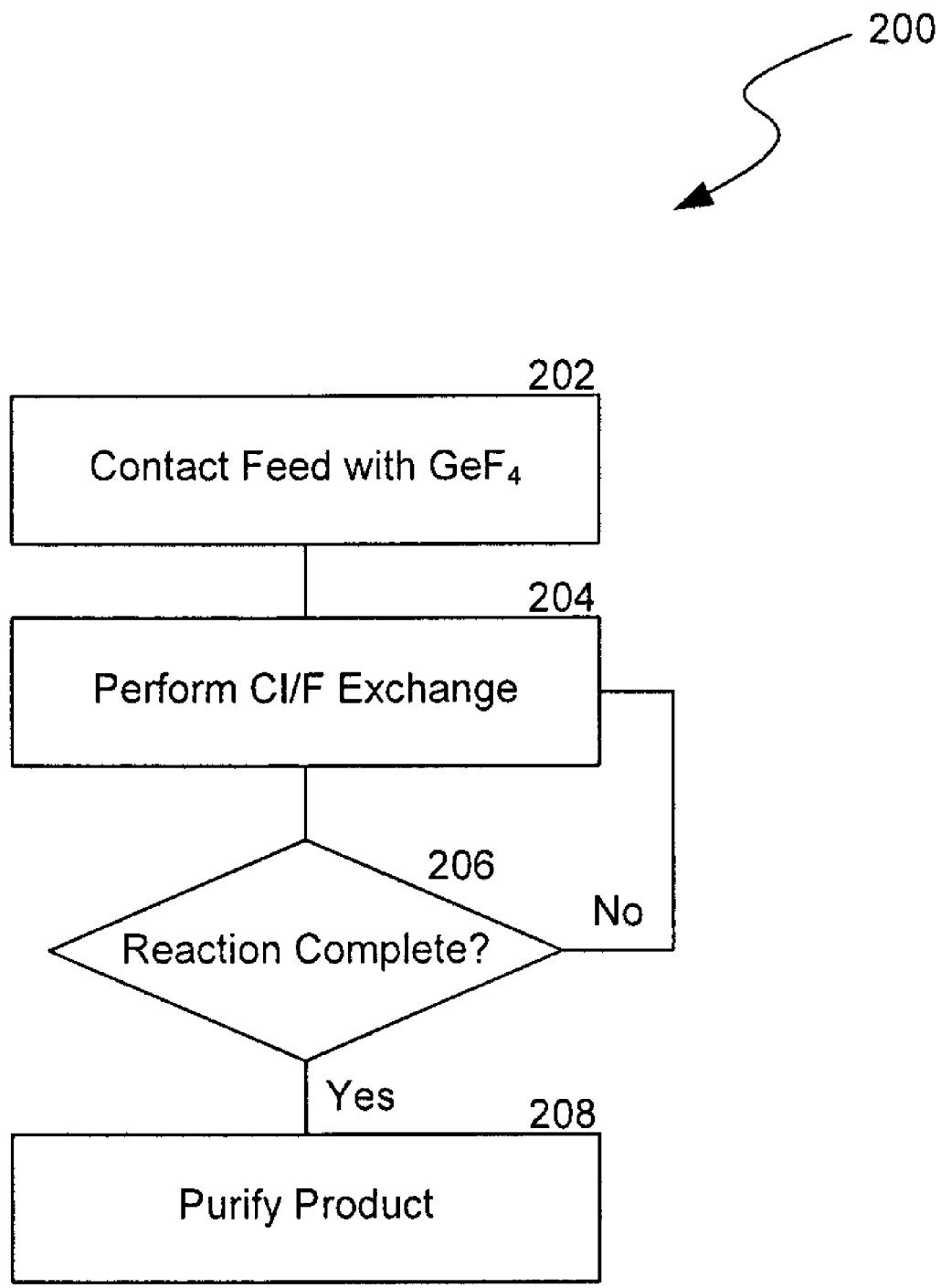
FIG. 3 is a flow chart illustrating a method for producing halocarbon compounds in accordance with an embodiment of the disclosure.

FIG. 3 is a flow chart illustrating a method 200 for producing halocarbon compounds (e.g., CFC-113, CFC-114a, and CFC-115) in accordance with an embodiment of the disclosure. The method 200 can include contacting a reaction feed containing a chlorocarbon compound (e.g., hexachloroethane) with a metal halide (e.g., $GeF_4$) in the presence of a catalyst (e.g., $AlCl_3$) at block 202. The molar ratio of $AlCl_3$/hexachloroethane/$GeF_4$ can be about 1:A:B (6<A<15 and 7<B<60). In one embodiment, the method 200 then includes performing a fluorination reaction (e.g., a chlorine-fluorine exchange reaction) on hexachloroethane at block 204 as follows:

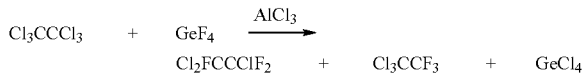

$$Cl_3CCCl_3 + GeF_4 \xrightarrow{AlCl_3} Cl_2FCCClF_2 + Cl_3CCF_3 + GeCl_4$$

In another embodiment, the fluorination reaction can also be as follows:

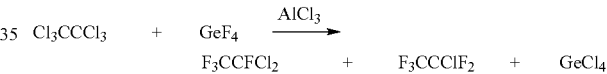

$$Cl_3CCCl_3 + GeF_4 \xrightarrow{AlCl_3} F_3CCFCl_2 + F_3CCClF_2 + GeCl_4$$

Suitable reaction temperatures can be about 220° to about 375° C., and suitable pressures can be about 500 to 800 psig.

A decision is made at block 206 to determine whether the reaction is complete. In one embodiment, the decision can be based on a reaction time (e.g., about six to eight hours). In another embodiment, the decision can be based on a conversion of the reaction and/or other reaction parameters. For example, an operator can periodically sample the material in the reactor 101 to determine a concentration of hexachloroethane. If the concentration of hexachloroethane is below a threshold, then the reaction is indicated to be complete.

If the reaction is complete, the method 200 further includes purifying the reaction product at block 208. Purifying the reaction product can include separating desired CFC compounds of the reaction product using condensation, distillation, liquid-liquid extraction, liquid-gas separation, and/or other suitable techniques. If the reaction is not complete, the process reverts to performing the chlorine-fluorine exchange on hexachloroethane at block 204.

EXAMPLES

Figure 4:
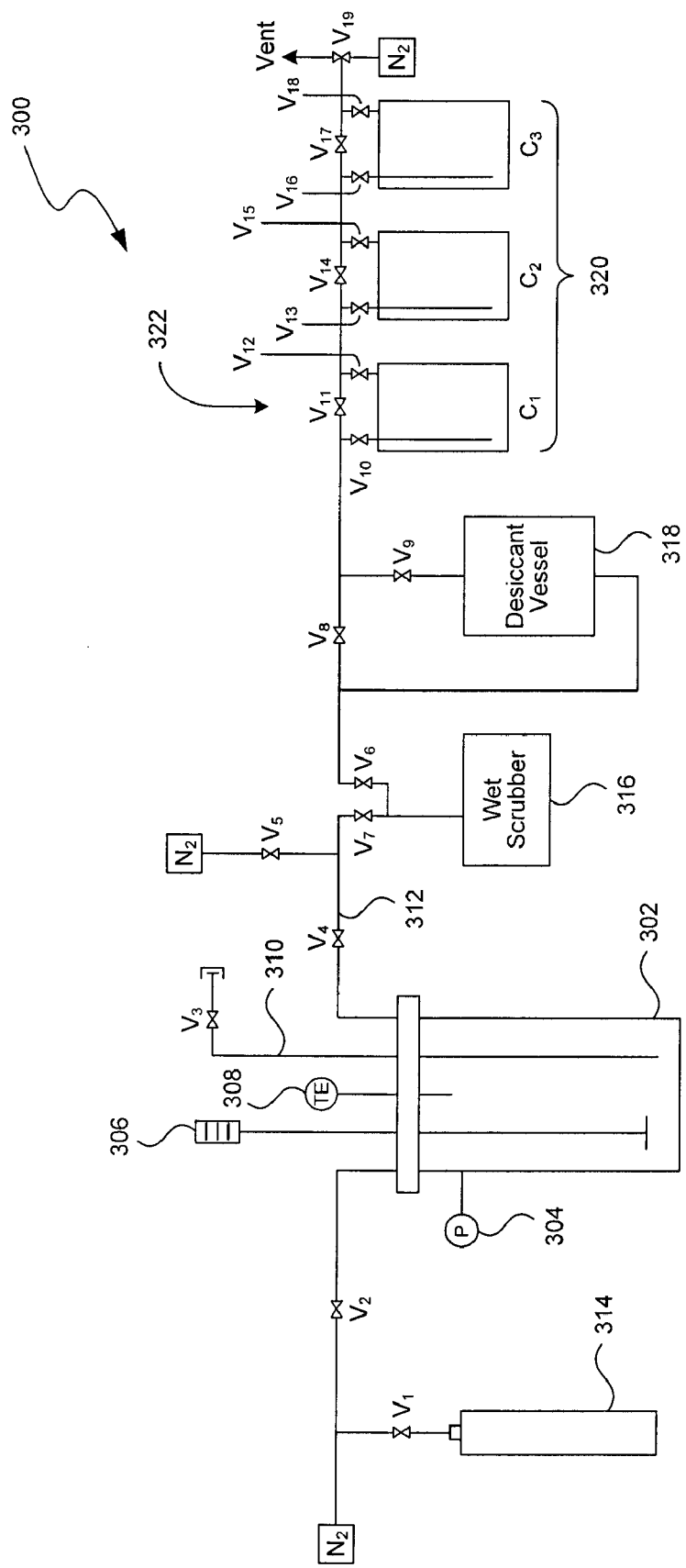
FIG. 4 is a schematic diagram illustrating a system for producing halocarbon compounds in accordance with an embodiment of the disclosure.

Experiments were conducted to fluorinate hexachloroethane using $GeF_4$ in the presence of $AlCl_3$ in a bench-top reactor (Model No. 4563) supplied by the Parr Instrument Company of Moline, Ill. FIG. 4 is a schematic diagram illustrating an experimental system 300 for producing halocarbon compounds in accordance with an embodiment of the disclosure.

As shown in FIG. 4, the system 300 includes an Inconel 600 reactor 302 having a volume of about 600 mL. The reactor 302 includes a pressure monitor 304, a mixer 306, and a temperature monitor 308. The reactor 302 also includes a liquid sample line 310 and a gas sample line 312. The system 300 also includes a cylinder 314 holding gaseous $GeF_4$ (187 psig at 21° C.). The system 300 also includes a 200 mL wet scrubber 316 containing KOH and a desiccant vessel 318 containing $Al_2O_3$ and KOH pellets. The system 300 further includes three 75 mL sample cylinders 320 (labeled $C_1$-$C_3$). The sample cylinders 320 can be held at various temperatures and pressures for collecting materials with different boiling points. Various components of the system 300 can be isolated using a plurality of valves 322 (labeled $V_1$-$V_{19}$).

All chemicals used in the following experiments were obtained commercially from Aldrich-Sigma, Inc. of Milwaukee, Wis. The $GeF_4$ gas was produced by International Isotopes Inc. of Idaho Falls, Id. Fourier transform infrared (FTIR) spectra were recorded on a MIDAC I1201 bench-top infrared spectrometer as neat liquids between potassium bromide (KBr) plates or gas samples in a 10 cm path-length demountable gas cell with zinc-selenium (ZnSe) windows. 1H, 13C, and 19F NMR spectra were obtained on a 300 MHz Bruker AMX spectrometer at 200, 50, and 188 MHz, respectively, by using $CDCl_3$ as a locking solvent. Chemical shifts were reported relative to $Me_4Si$ or $CFCl_3$. GCMS spectra were obtained with a Shimadzu Q5050 spectrometer (EI-mode). Elemental analyses were performed by the Desert Analytics Laboratory of Tucson, Ariz.

Experiment I

Solid hexachloroethane (44.5 g, 0.190 mol) and solid aluminum chloride (4.0 g, 0.030 mol) were charged into the reactor 302. The reactor 302 was then closed and bolted. Germanium tetrafluoride (32.3 g, 0.217 mol) was fed into the reactor 302 at 19° C. in a vented hood. The pressure in the reactor 302 was 130 psig. The gas-in and gas-out valves on the reactor 302 were closed to isolate the contents in the reactor 302, and the supply sample line was purged several times and disconnected. The reactor 302 was then transferred into a heating mantle and connected onto a manifold with the scrubber 316, the desiccant vessel 318, and the sample cylinders 320 for cryogenic distillation. The contents in the reactor 302 were stirred and heated to about 220° C. for about one hour, about 250° C. for about one hour, and at 310° C. for about six hours. The reactor pressure rose to about 518 psig at 310° C. After eight hours, the reactor 302 was slowly cooled to room temperature (approximately 15° C.), and the pressure dropped to about 47 psig. The gaseous reaction products, including unreacted $GeF_4$, were vented through the gas-out valve to the scrubber 316 until the pressure in the reactor 302 dropped to about 0 psig. Germanium halide byproducts were recovered as insoluble germanium (IV) oxide. Subsequently, the reactor 302 was pressurized several times with nitrogen to about 90 psig and vented through the scrubber 316. Subsequently, the reactor 302 was pressurized several times with nitrogen, to 90 psig, and vented through the scrubber 316. Thereafter, the reactor 302 was opened in a vented hood. About 56.6 grams of liquid were poured from the reactor 302 into a 100 mL high density polyethylene (HDPE) plastic container. About 5 grams of brown solid residue were observed around the bottom of the reactor 302. The liquid product was poured into 60 mL of deionized water in a polypropylene separating funnel. About 26.3 grams of non-fuming light brown liquid were separated and dried with 4 grams of magnesium sulfate ($MgSO_4$) in a 100 mL glass flask and then analyzed by FTIR, 19F NMR, and GCMS.

Experiment II

Experiment II was carried out following a procedure similar to that of Experiment I with a different molar ratio of the reagents and a different reaction temperature than those used in Experiment I. In particular, solid hexachloroethane (30.2 g, 0.127 mol) and solid aluminum chloride (4.0 g, 0.030 mol) were charged into the reactor 302, and a reaction temperature of 340° C. was used. $GeF_4$ gas (49.5 g, 0.333 mol) was then fed into the reactor 302. The reactor 302 was then heated to 340° C., and the pressure in the reactor 302 rose to about 747 psig. After about eight hours, the reactor 302 was slowly cooled to room temperature. As a result, the pressure dropped to about 110 psig at about 21° C.

Experimental Results

Figure 5:
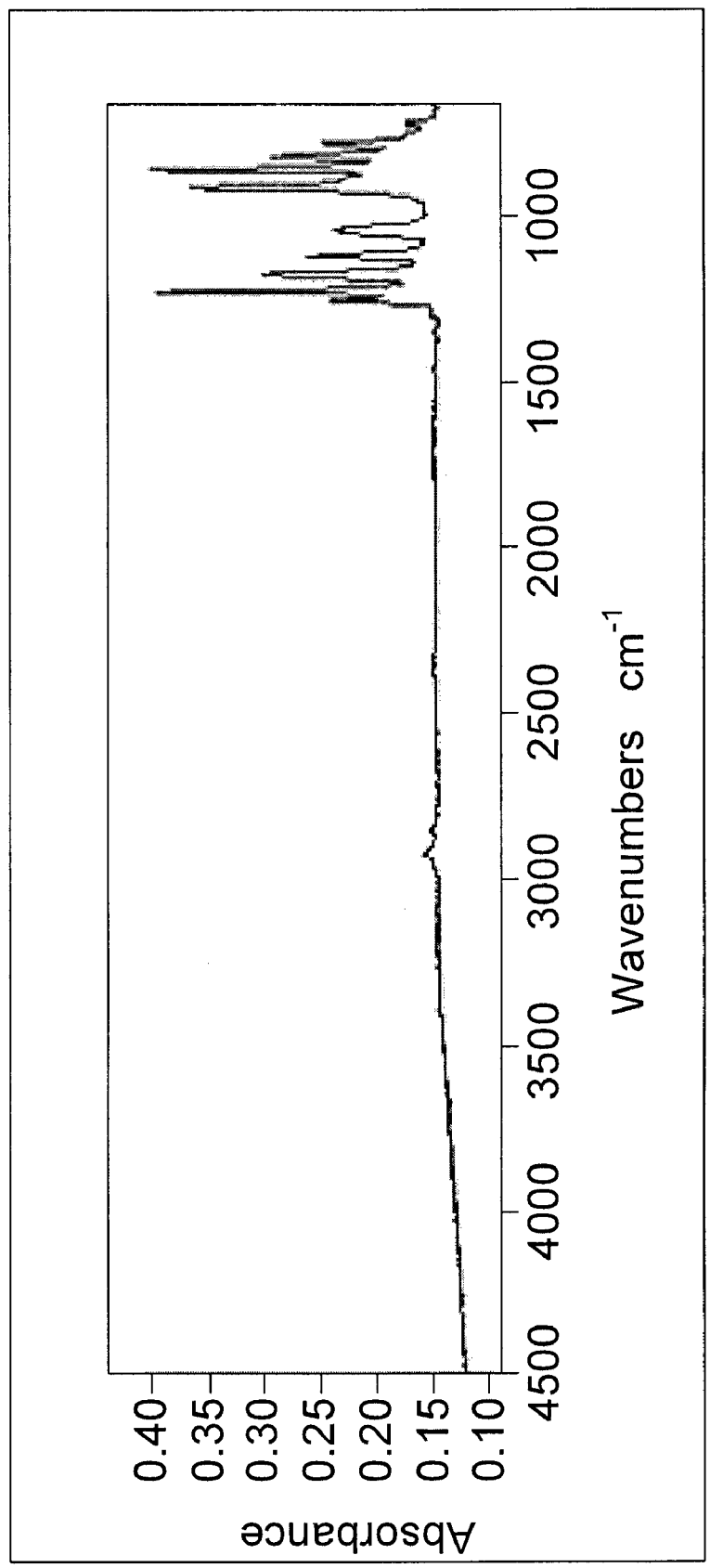
FIG. 5 is a Fourier transform infrared (FTIR) scan of a reaction product prepared in accordance with an embodiment of the disclosure.
Figure 6:
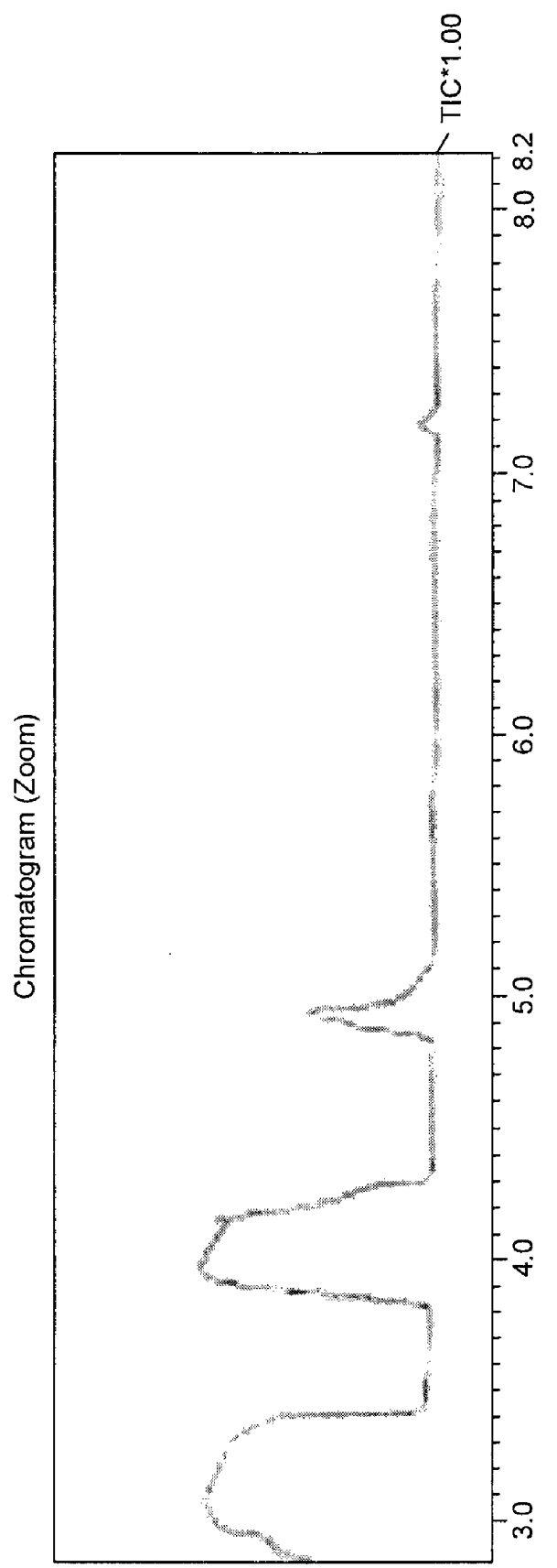
FIG. 6 is a gas chromatography of a reaction product prepared in accordance with an embodiment of the disclosure.
Figure 7:
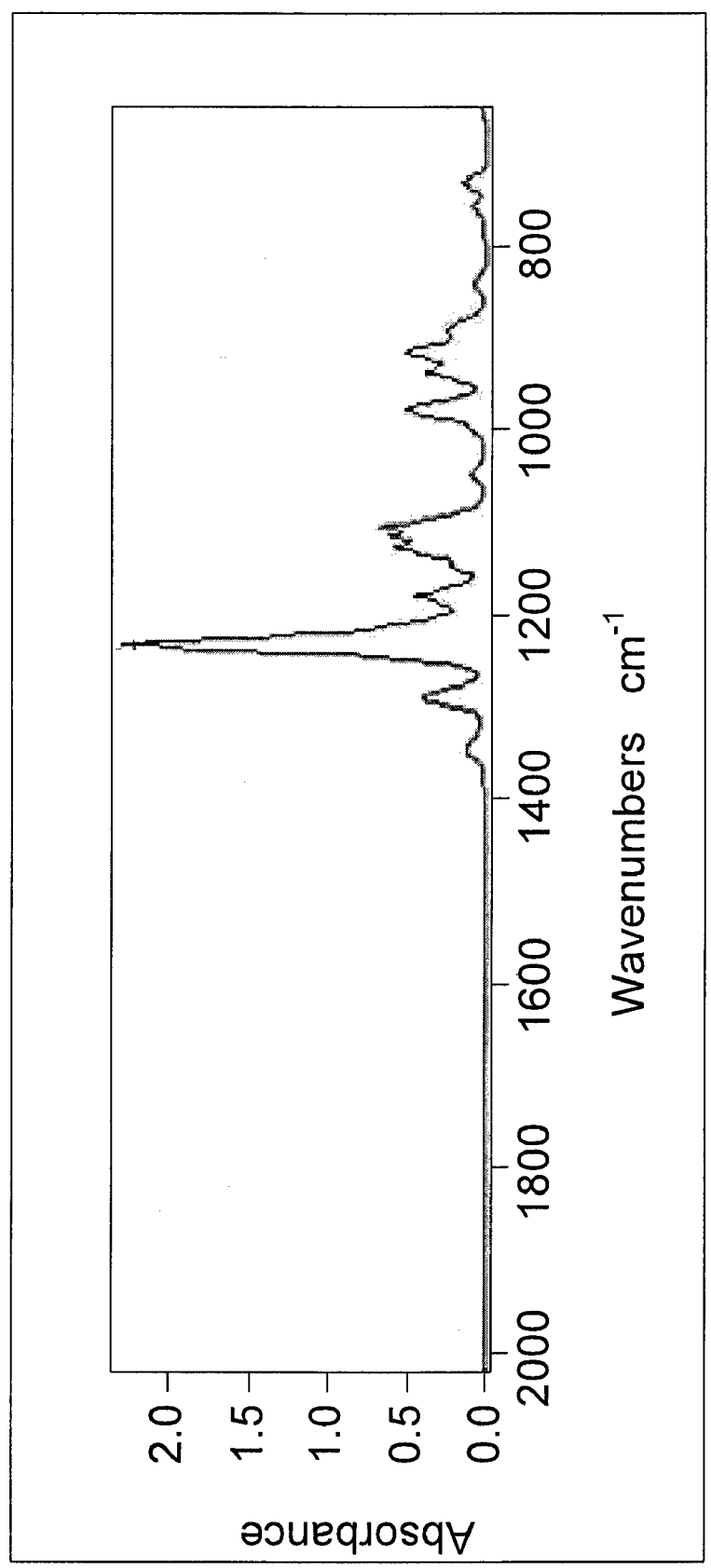
FIG. 7 is a Fourier transform infrared (FTIR) scan of a reaction product prepared in accordance with another embodiment of the disclosure.
Figure 8:
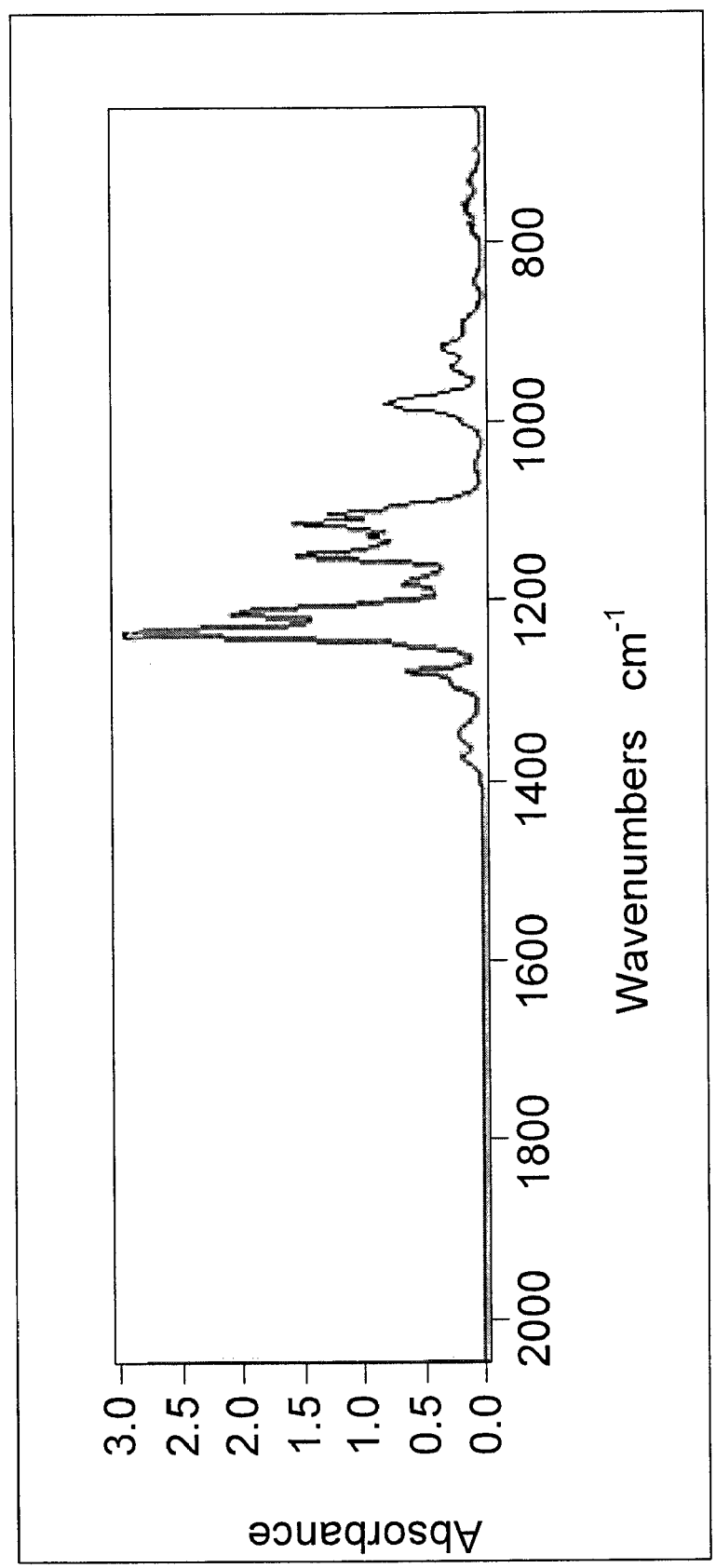
FIG. 8 is a Fourier transform infrared (FTIR) scan of a reaction product prepared in accordance with another embodiment of the disclosure.

In Experiment I and Experiment II, hexachloroethane reacted readily with $GeF_4$ in the presence of a superacid and/or a Lewis acid catalyst. As shown in the FTIR analysis and gas chromatography results in FIGS. 5 and 6, the reaction product in Experiment I contained about 53% CFC-113. The identification of the isomer product was based on the correlation of the coupling constant of the triplet and doublet signals in the $^{19}F$ NMR spectrum of the reaction product. The gaseous product did not have characteristics of any expected fluorocarbon products. The conversion of hexachloroethane was about 75%. As shown in the FTIR analyses in FIGS. 7 and 8, the reaction product in Experiment II contained about 73% CFC-114a, and about 27% CFC-115. The conversion of hexachloroethane was about 98%

From the foregoing, it will be appreciated that specific embodiments of the invention have been described herein for purposes of illustration, but that various modifications may be made without deviating from the invention. Elements of one embodiment may be combined with other embodiments in addition to or in lieu of the elements of the other embodiments. Accordingly, the invention is not limited except as by the appended claims.

I claim:

1. A method for producing chlorofluorocarbon compounds, comprising reacting 1,1,1,2,2,2-hexachloroethane ($Cl_3CCCl_3$) with germanium tetrafluoride ($GeF_4$) in the presence of an aluminum (Al) halide.

2. The method of claim 1 wherein reacting 1,1,1,2,2,2-hexachloroethane with germanium tetrafluoride includes reacting 1,1,1,2,2,2-hexachloroethane with germanium tetrafluoride in the presence of aluminum trichloride ($AlCl_3$).

3. The method of claim 2 wherein reacting 1,1,1,2,2,2-hexachloroethane with germanium tetrafluoride includes reacting 1,1,1,2,2,2-hexachloroethane with germanium tetrafluoride in the presence of aluminum trichloride at a temperature of about 220° to about 375° C.

4. The method of claim 2, further comprising forming at least one of aluminum chlorodifluoride ($AlClF_2$), aluminum dichlorofluoride ($AlCl_2F$), and aluminum trifluoride ($AlF_3$) when reacting 1,1,1,2,2,2-hexachloroethane with germanium tetrafluoride.

5. The method of claim 4, further comprising shifting the equilibrium toward aluminum trifluoride.

6. The method of claim 2 wherein reacting 1,1,1,2,2,2-hexachloroethane with germanium tetrafluoride includes reacting 1,1,1,2,2,2-hexachloroethane with germanium tetrafluoride at a molar ratio of germanium tetrafluoride to 1,1,1,2,2,2-hexachloroethane of about 1.16 to 1.

7. The method of claim 2, further comprising producing at least one of 1,1,2-trichloro-1,2,2-trifluoroethane ($CCl_2FCClF_2$), 1,1,1-trichloro-2,2,2-trifluoroethane ($CCl_3CF_3$), 1,2-dichloro-1,2,2,2-tetrafluoroethane ($CCl_2FCF_3$), and 1-chloro-1,1,2,2,2-pentafluoroethane ($CClF_2CF_3$) by reacting 1,1,1,2,2,2-hexachloroethane with germanium tetrafluoride.

8. A method for producing chlorofluorocarbon compounds, comprising contacting a reaction feed containing 1,1,1,2,2,2-hexachloroethane ($Cl_3CCCl_3$) and germanium tetrafluoride ($GeF_4$) with a catalyst containing an aluminum (Al) halide in a reactor, to thereby produce a reaction product containing at least one of 1,1,2-trichloro-1,2,2-trifluoroethane ($CCl_2FCClF_2$) and 1,1,1-trichloro-2,2,2-trifluoroethane ($CCl_3CF_3$).

9. The method of claim 8 wherein contacting a reaction feed includes contacting the reaction feed with a catalyst bed of the reactor, the catalyst bed holding a catalyst containing aluminum trichloride ($AlCl_3$).

10. The method of claim 8 wherein reacting 1,1,1,2,2,2-hexachloroethane with germanium tetrafluoride includes performing chlorine-fluoride exchange on 1,1,1,2,2,2-hexachloroethane of the reaction feed in the presence of the catalyst.

11. The method of claim 8 wherein reacting 1,1,1,2,2,2-hexachloroethane with germanium tetrafluoride includes reacting 1,1,1,2,2,2-hexachloroethane with germanium tetrafluoride at a temperature of about 220° C. to about 375° C. and a pressure of about 500 to about 800 psig.

12. The method of claim 8 wherein the metal halide includes aluminum trichloride ($AlCl_3$), and wherein reacting 1,1,1,2,2,2-hexachloroethane with germanium tetrafluoride includes reacting ,1,1,1,2,2,2-hexachloroethane with germanium tetrafluoride at a molar ratio of aluminum chloride/1,1,1,2,2,2-hexachloroethane/germanium tetrafluoride of about 1:6:7.

13. The method of claim 8 wherein reacting 1,1,1,2,2,2-hexachloroethane with germanium tetrafluoride includes reacting 1,1,1,2,2,2-hexachloroethane with germanium tetrafluoride while germanium tetrafluoride is in molar excess over 1,1,1,2,2,2-hexachloroethane, and wherein the method further includes scrubbing excess germanium tetrafluoride with a material containing a base.

14. The method of claim 8, further comprising distilling the produced reaction product containing at least one of 1,1,2-trichloro-1,2,2-trifluoroethane ($CCl_2FCClF_2$) and 1,1,1-trichloro-2,2,2-trifluoroethane ($CCl_3CF_3$).

15. A method for producing chlorofluorocarbon compounds, comprising:
loading a charge containing 1,1,1,2,2,2-hexachloroethane ($Cl_3CCCl_3$) and aluminum trichloride ($AlCl_3$) into a reactor;
flowing a feed gas containing germanium tetrafluoride ($GeF_4$) into the reactor holding the charge containing 1,1,1,2,2,2-hexachloroethane ($Cl_3CCCl_3$) and aluminum trichloride; and
reacting 1,1,1,2,2,2-hexachloroethane of the charge with germanium tetrafluoride of the feed gas in the presence of aluminum trichloride in the reactor.

16. The method of claim 15, further comprising discharging a product containing at least one of 1,1,2-trichloro-1,2,2-trifluoroethane ($CCl_2FCClF_2$) and 1,1,1-trichloro-2,2,2-trifluoroethane ($CCl_3CF_3$) from the reactor.

17. The method of claim 16, further comprising collecting the product in a cylinder cooled with liquid nitrogen.

18. The method of claim 15, further comprising heating the reactor to a temperature of about 220° C. to about 375° C. before flowing the feed gas into the reactor.

19. The method of claim 15 wherein reacting 1,1,1,2,2,2-hexachloroethane of the charge with germanium tetrafluoride of the feed gas includes reacting 1,1,1,2,2,2-hexachloroethane with germanium tetrafluoride with a conversion greater than about 70%.

20. The method of claim 15 wherein reacting 1,1,1,2,2,2-hexachloroethane of the charge with germanium tetrafluoride of the feed gas includes reacting 1,1,1,2,2 2-hexachloroethane with germanium tetrafluoride with a conversion greater than about 70% and a selectivity greater than about 50% for 1,1,2-trichloro-1,2,2-trifluoroethane ($CCl_2FCClF_2$).

21. A method for producing chlorofluorocarbon compounds, comprising:
contacting a first reagent containing 1,1,1,2,2,2-hexachloroethane ($Cl_3CCCl_3$) with a second reagent containing germanium tetrafluoride ($GeF_4$) in the presence of a catalyst containing aluminum trichloride ($AlCl_3$);
concurrently forming a series of equilibria between species of $AlCl_xF_y$ (x+y=3) and species of $GeCl_aF_b$ (a+b=4), as follows:

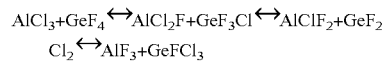

$$Cl_2 \leftrightarrow AlF_3 + GeFCl_3$$

fluorinating 1,1,1,2,2,2-hexachloroethane in the first reagent with germanium tetrafluoride in the second reagent while catalyzed by the species of $AlCl_xF_y$ (x+y=3).

22. The method of claim 21 wherein fluorinating 1,1,1,2,2,2-hexachloroethane includes shifting the series of equilibria to produce a product from the reaction with a selectivity toward at least one of 1,1,2-trichloro-1,2,2-trifluoroethane ($CCl_2FCClF_2$), 1,1-dichloro-1,2,2-trifluoroethane ($CCl_2FCHF_2$), and 1-chloro-1,1,2,2,2-pentafluoroethane ($CClFCF_3$).

23. The method of claim 21 wherein performing a reaction includes performing a reaction between 1,1,1,2,2,2-hexachloroethane in the first reagent and germanium tetrafluoride in the second reagent while catalyzed by the species of $AlCl_xF_y$ (x+y=3) at a temperature of about 310° C. and a molar ratio of 1,1,1,2,2,2-hexachloroethane to germanium tetrafluoride of about 1:1.67, and wherein selectively producing a product includes producing a product containing at least about 50% 1,1,2-trichloro-1,2,2-trifluoroethane ($CCl_2FCClF_2$).

24. The method of claim 21 wherein performing a reaction includes performing a reaction between 1,1,1,2,2,2-hexachloroethane in the first reagent and germanium tetrafluoride in the second reagent while catalyzed by the species of $AlCl_xF_y$ (x+y=3) at a temperature of about 340° C. and a molar ratio of 1,1,1,2,2,2-hexachloroethane to germanium tetrafluoride of about 1:2.75, and wherein selectively producing a product includes producing a product substantially consisting of 1,1-dichloro-1,2,2-trifluoroethane ($CCl_2FCH F_2$) and 1-chloro-1,1,2,2,2-pentafluoroethane ($CClFCF_3$).

25. The method of claim 21 wherein performing a reaction includes performing a reaction between 1,1,1,2,2,2-hexachloroethane in the first reagent and germanium tetrafluoride in the second reagent while catalyzed by the species of $AlCl_xF_y$ (x+y=3) at a temperature of about 340° C. and a molar ratio of 1,1,1,2,2,2-hexachloroethane to germanium tetrafluoride of about 1:2.75, and wherein selectively producing a product includes producing a product containing about 73% 1,1-dichloro-1,2,2-trifluoroethane ($CCl_2FCHF_2$) and about 23% 1-chloro-1,1,2,2,2-pentafluoroethane ($CClFCF_3$).

* * * * *